United States Patent [19]

Haglund

[11] Patent Number: 4,994,487

[45] Date of Patent: Feb. 19, 1991

[54] METHODS AND COMPOSITIONS FOR THE TREATMENT OF PLANTS

[75] Inventor: William A. Haglund, Burlington, Wash.

[73] Assignee: Washington State University Research Foundation, Pullman, Wash.

[21] Appl. No.: 412,883

[22] Filed: Sep. 26, 1989

[51] Int. Cl.$^5$ ................... A01N 47/10; A61K 31/27
[52] U.S. Cl. ..................................................... 514/476
[58] Field of Search ........................................ 514/476

[56] References Cited

U.S. PATENT DOCUMENTS

| | | | |
|---|---|---|---|
| 2,614,957 | 10/1952 | Somerville | 167/22 |
| 2,614,959 | 10/1952 | Somerville | 167/22 |
| 2,766,554 | 10/1956 | Dorman | 71/101 |
| 2,776,922 | 1/1957 | Somerville | 167/33 |
| 2,792,327 | 5/1957 | Hunt | 167/22 |
| 2,835,625 | 5/1958 | Lo et al. | 167/22 |
| 3,699,231 | 10/1972 | Werlein et al. | 424/286 |
| 3,836,655 | 9/1974 | Kensler et al. | 424/286 |
| 4,708,879 | 11/1987 | Huber | 426/335 |

OTHER PUBLICATIONS

"Vapam, Soil Fumigant Solution For All Crops", Stauffer Chemical Company, Westport, CT, pp. 210–212.

Fischer, B. B. et al., "The User of Metham for Weed Control, A Progress Report", *Runcina* 41:1–17, 1989.

Jaworski, C. A. et al., "Response of Onions Grown for Transplants to Soil Fumigation", *J. Amer. Soc. Hort. Sci.* 103(3):385–388, 1978.

Johnson, A. W. et al., "Effects of Film Mulch, Trickle Irrigation, and Soil Pesticides on Nematodes and Yield of Polebean", *Plant Disease Reporter*, 63(5):360–364, 1979.

Toyama, Aki, CA 99:117707w 1983.
Jaworski, CA, CA89:37926v 1978.
Johnson, AW, CA91:85121s 1979.

*Primary Examiner*—Douglas W. Robinson
*Assistant Examiner*—R. Travers
*Attorney, Agent, or Firm*—Christensen, O'Connor, Johnson & Kindness

[57] ABSTRACT

Crop yields in a plant bed are significantly enhanced by treating soil in the plant bed with a fungicidally effective amount of metham, the fungicidally effective amount being insufficient to retard growth of a plant. In the practice of the invention, the plant soil is treated with metham by dripping an aqueous solution of metham into a seed furrow, by injecting the aqueous solution into the soil or by drenching the soil with the aqueous solution, either at about the time of planting of the seed or vegetative material or by treatment of the soil surrounding established plant crops. Significantly reduced amounts of metham are employed to reduce damage to the planted seed or vegetative material.

12 Claims, No Drawings

METHODS AND COMPOSITIONS FOR THE TREATMENT OF PLANTS

FIELD OF THE INVENTION

This invention relates to methods and compositions for the fungicidal treatment of soil to enhance seed germination, seedling development and plant growth.

BACKGROUND OF THE INVENTION

Metham sodium (sodium methyldithiocarbamate, also know as metam sodium, metam and metham, and marketed under the names Metam, Sectagon II, Soil-Prep, Vapam and V.P.M.) is commercially available for use as a preplanting soil fumigant solution for plant crops. After application to the soil, the liquid solution is converted into a gaseous fumigant, methyl isothiocyanate, which is known to be effective as a fungicide, pesticide and herbicide for the control of weeds, germinating weed seeds and insects, such as Henbit, Lambsquarters, Pigweed, Careless weed, Watergrass, Johnsongrass, Nutgrass, Wild morning-glory, Purslane, Nematodes, Symphylids, and as a pesticide/fungicide for the control of soil-borne diseases, such as Rhizoctonia, Phythium, Phytophora, Vericillium, Sclerotinia, Oat root fungus and Club root of crucifers. In a 32.7% aqueous solution (3.18 pounds by dry weight of active ingredient per gallon), metham sodium is applied as a preplanting fumigant at application rates of 50–100 gallons (159–318 pounds by dry weight of active ingredient)per acre.

Due to its highly toxic nature, planting may not take place until 14–21 days after conventional metham sodium application for well-drained soils of light-to-medium texture, for 30 days after conventional treatment for soils that are heavy or especially high in organic matter (or that remain wet and/or cold), or until at least 60 days after conventional treatment where metam sodium dosages greater than 100 gallons per acre have been applied.

The fumigant and/or fungicidal activity of metham sodium and biologically active derivatives and analogs of metham sodium have been known in the art for some time. For example, U.S. Pat. No. 2,614,957 discloses a fungicidal composition containing about 75:99% by weight of a metham sodium analog, sodium dimethyldithiocarbamate, and about 25:1% by weight of the sodium salt of 2-mercaptobenzothiozol.

U.S. Pat. Nos. 2,614,959 and 776,922 disclose the fungicidal activity of compositions of the zinc salt of dimethyldithiocarbamate combined with the ferric or zinc salt of mercaptobenzothiozol.

U.S. Pat. No. 2,792,327 discloses a method of controlling fungus infestation by applying sodium monomethyl dithiocarbamate directly to the locus of the vegetation to be treated for fungus control. In practice, metham sodium is applied in a foliar application to plant leaves or as a preplant seed treatment. It is stated that the method can be used to treat living plants, such as crop plants, ornamental plants, fruit bearing trees, and plant seeds. Suitable application rates are stated to be about 1 to 4 pounds per acre for use as a foliar spray, about 0.5–3 oz. per 100 pounds of seed to be treated, or about 0.005 to 0.02 pounds of sodium monomethyl dithiocarbamate per pound of organic matter treated.

U.S. Pat. No. 2,835,625 discloses a fungicidal metham sodium derivative, isopropoxycarbonyl dimethyldithiocarbamate.

U.S. Pat. No. 3,699,231 discloses the use of a mixture of metham sodium and formaldehyde in a 1/1 weight ratio to inhibit the growth of bacteria, such as in drilling fluids.

In addition, metham sodium has been used in the art in connection with the preservation of harvested crops. For example, U.S. Pat. No. 3,836,655 discloses a composition of metham sodium and propionic acid for use in preserving moist grain during storage. U.S. Pat. No. 4,708,879 discloses the use of metham sodium for preserving high moisture forage crops, such as hay, to prevent microbial degradation during storage.

The use of metham sodium as a preplanting herbicide applied through sprinkler systems, low-volume drip irrigation systems, subsurface blading and as a drench, is described in detail in Fischer et al., "The Use of Metham For Weed Control—A Progress Report," *Runcina*, Vol. 41, University of California Cooperative Extension, Fresno County, pp. 1–17 (1989). Its use as a herbicide, fungicide and nematocide has continued essentially unchanged for at least the last 30 years. While the soil fumigant and fungicidal properties of metham sodium are well known in the art, its highly toxic nature presents difficulties when used in connection with crop planting for fungicidal purposes. For example, as conventionally applied, a significant amount of time ranging from about 7 days to about 60 days must elapse prior to crop planting in order to prevent metham sodium damage to the newly planted crop. This results not only in significant time delays between fungicide application and crop planting, but also requires multiple pass working of the crop field. In addition, the relatively high cost of metham sodium makes conventional application prohibitively expensive for marginal application conditions.

SUMMARY OF THE INVENTION

It has now been discovered that the foregoing problems can be overcome and that crop yields in a plant bed can be significantly enhanced by treating soil in the plant bed with a fungicidally effective amount of metham at about the time of planting of the seed and/or vegetative material in the plant bed, the fungicidally effective amount being insufficient to retard growth of a plant from the seed or vegetative material. In the practice of the invention, the plant soil is treated with metham by dripping an aqueous solution of metham into a seed furrow, by injecting the aqueous solution into the soil or by drenching the soil with the aqueous solution, either at about the time of planting of the seed or vegetative material or by treatment of the soil surrounding established plant crops. Significantly reduced amounts of metham are employed to reduce damage to the planted seed or vegetative material. It has surprisingly been found that metham retains sufficient fungicidal activity when employed in the practice of the present invention to significantly enhance crop yields without significantly retarding germination of the seed or growth of the plant crops.

DETAILED DESCRIPTION OF THE INVENTION

In accordance with the present invention, soil in a plant bed is treated, either at about the time of planting of plant seed or plant reproductive vegetative material in the plant bed or by treatment of the soil surrounding established plant crops, by contacting the soil with a fungicidally effective amount of metham, the amount being insufficient to significantly reduce or retard the rate of seed germination and/or plant growth.

Metham, when formulated in aqueous solution at about 3.0-3.5 pounds of active ingredient per gallon, is a nonvolatile material. However, upon contact with soil, metham chemically decomposes to produce methyl isothiocyanate, a volatile, highly toxic gas. Decomposition of metham to methyl isothiocyanate typically occurs within about 5 hours of treatment of the soil. Thereafter, the methyl isothiocyanate further decomposes in the soil to nontoxic compounds.

As used herein, the term "metham" includes methyldithiocarbamate and its fungicidally effective salts. In a presently particularly preferred embodiment, metham is used in the form of sodium N-methyl dithiocarbamate dihydrate (metham sodium), although it is to be understood that other analogues or salts of N-methyldithiocarbamate, such as potassium N-methyldithiocarbamate are included in the term metham and may be employed in the practice of the invention.

Since the amounts of metham used to treat soil in accordance with the invention are substantially less than those conventionally used to obtain herbicidal, fungicidal and nematocidal activity, a significant advantage of the invention is the ability to be able to treat soil in a seed bed at or about the time of planting, as opposed to 10-60 days prior to planting using conventional techniques. As used herein, the term "at or about the time of planting" includes methods of treatment in which the soil in a seed bed is treated with an aqueous solution of metham either as the seed or vegetative material is being planted in the soil or shortly before or after planting. Accordingly, the active aqueous solution may be dripped or sprayed into a seed furrow in the seed bed as the seed or vegetative material is being planted, may be injected in the soil beneath the seed or vegetative material during planting, or the soil in the seed bed may be drenched with the aqueous solution shortly prior to, during or shortly following planting of the seed or vegetative material in the soil.

In one presently preferred embodiment, soil is treated in accordance with the invention at about the time of planting. In other embodiments, established plant crops may be advantageously affected by treatment of the soil surrounding the plant crops. Accordingly, practice of the invention is broadly applicable to a variety of seeds, reproductive vegetative material, seedlings and established plants. Representative, illustrative crops which may be advantageously treated at the time of seed planting include, for example, dry beans, dry peas, soy beans, sweet corn, field corn, green beans, green peas, cotton, wheat, barley, lentils, and the like. Representative, illustrative crops which may be advantageously treated at the time of planting of reproductive vegetative material include, for example, potatoes, pineapple, flower bulbs, and the like. Representative, illustrative plants and/or seedlings which may be treated in accordance with the invention include container grown ornamentals, fruit trees, vegetable seedlings, turf grass and the like.

The precise amount of metham to be applied to a particular plant crop in accordance with the invention will depend upon the sensitivities of the particular crop, the method of application, and other field conditions. Generally, however, metham is applied in the form of an aqueous solution in amounts equivalent to about 0.003 to about 1.0 g of metham by dry weight of active ingredient per linear meter of planting furrow for applications where the aqueous solution is applied to the soil in the seed furrow at the time of planting of seed or vegetative material, at a rate equivalent to about 0.015 to about 1.5 g of metham by dry weight per linear meter of plant row for those applications where the aqueous solution is injected into the soil beneath the seed or vegetative material at about the time of planting, or at a rate of about 30 to about 2,500 ppm of metham by dry weight of active ingredient in aqueous solution for those applications where the soil is drenched or vegetative material is directly contacted with the aqueous solution.

These and other embodiments in the invention may be better understood in connection with the following representative examples, which are presented for purposes of illustration of the invention and not by way of limitation.

EXAMPLE 1

Drip Application in Seed Furrow

The effect of application of metham in the seed furrow at time of seeding of the crop was determined in the following manner. A dilute aqueous solution of metham was prepared by mixing one part of metham (VAPAM, Stauffer Chemical Company, Westport, Conn., U.S.A., 3.18 pounds/gallon of active material) with nine parts of water. A seed bed was prepared in Skagit County, Wash., U.S.A., and planted in rows with 1 meter spacing with seed of field corn, green peas, green beans and dry peas. Test sections for each crop consisted of a single 6 meter row, with 4 replicates for each metham treatment level for each crop. At the time of planting of the seed, the dilute aqueous metham was metered into the seed row through a ¼ inch (inside diameter) polyethylene tube tipped with a flexible rubber tube that was set in the planter to drag on the bottom of the seed furrow. The rates of application were varied to determine the effect on crop yields, and are listed in Table I as weight of metham (active ingredient) per unit length of row treated. The crops were allowed to grow for the number of days indicated in Table 1, and then 2 meter sections from each replicate were harvested and weighed for total green weight. The results are shown in Table 1 as the average yield (green weight) per meter of row.

TABLE 1

| Rate of Application | | Average yield in grams/ meter of row | | | |
|---|---|---|---|---|---|
| grams/ meter | Ounces/ 1000 ft | Field corn | Green peas | Green beans | Dry peas |
| 0 | 0 | 821 | 350 | 306 | 252 |
| 0.0312 | 0.335 | 1003 | 383 | 400 | 340 |
| 0.0624 | 0.671 | 1093 | 473 | 383 | 340 |
| 0.1249 | 1.344 | 1030 | 287 | 240 | 525 |
| 0.2499 | 2.688 | 700 | 100 | 73 | 315 |
| 0.4998 | 5.375 | 590 | 23 | 0 | 67 |
| Growth period (days) | | 34 | 39 | 33 | 27 |

EXAMPLE 2

The effect of varying rates of metham application for the control of seedling diseases of peas was determined as follows. A greenhouse growing medium (Rediearth plus vermiculite 50:50, mix) was inoculated with 2 g of disease-infested field soil (known to contain Fusarium, Pythium, and Aphanomyces) per 100 cc of medium, and one crop of peas was grown in the medium to increase the natural disease level of the original field soil. The inoculated medium was then placed in 15.24 cm plastic pots and a 30.48 cm row (seed furrow) was marked in each pot. Green pea seeds, Puget variety, were planted in the medium in the seed furrow (10 seeds per pot), metham was applied in an aqueous solution to the seed furrow in an amount equivalent to 1.64 ml per meter of row, and then the seed furrow was immediately covered with 2.5 cm of the disease-infested growing medium. Varying concentrations of metham were employed, as shown in Table 2, with rates of application listed as dry weight of metham per unit length of row treated. Each pot was a single replication with 5 replicates being made at each treatment level. After 39 days, the plants in each pot were harvested by cutting at ground level and the plant yield (green weight) for each replicate (pot) was determined. The results are shown in the following Table 2.

TABLE 2

| Rate of Application | | Average* emergence seedlings | Average Yield (grams) | |
|---|---|---|---|---|
| Grams/ meter row | Ounces/ 1000 ft | | Per Pot | Per Plant |
| 0 | 0 | 8.2 | 6.9 | 0.83 |
| 0.00312 | 0.0335 | 8.7 | 8.6 | 0.98 |
| 0.00624 | 0.0671 | 8.7 | 7.9 | 0.90 |
| 0.01249 | 0.1344 | 8.7 | 8.5 | 0.97 |
| 0.02499 | 0.2688 | 9.5 | 10.0 | 1.05 |
| 0.06248 | 0.671 | 9.7 | 9.5 | 1.00 |
| 0.12496 | 1.344 | 9.0 | 9.1 | 0.93 |

*Average seedling emergence based on 19 seeds planted

EXAMPLE 3

Injection Application Below Seed Furrow

The effect of applying metham by injection below the seed furrow at time of seeding of the crop was determined by injecting an aqueous solution of metham 20 cm below the soil surface in a field seed bed in Skagit County, Wash., U.S.A., using rigid shanks (⅜ by 1½ by 24 inches) equipped with a small diamond shaped point. At the time of soil injection of the aqueous solution, pea seeds were planted in a seed furrow having a depth of 2.5 cm below the soil surface and located directly over the metham injection line. The rates of metham application were varied to determine the effect on plant yield, and are listed in Table 3 as weight of metham (active ingredient) per unit length of row treated. Each replicate consisted of a single row 6 meters in length, with 4 replications being made at each metham treatment level and rows being spaced 1 meter apart. After 92 days, 2 meter sections from each replicate were harvested and weighed for total green weight. The results are shown in Table 3 as the average yield (green weight) per plant.

TABLE 3

Average green weight in grams/plant harvested from two meters of row.

| Applicate Rate | | Yield (grams) | |
|---|---|---|---|
| Grams/ meter | Ounces/ 1000 ft | Plant weight | Pod weight |
| 0 | 0 | 147 | 78 |
| 0.0624* | 0.671* | 220* | 113* |
| 0.0624 | 0.671 | 219 | 112 |
| 0.1249 | 1.344 | 211 | 95 |
| 0.1874 | 1.874 | 172 | 86 |

*Application of aqueous solution of metham in the seed furrow at time of planting, a comparison to injection.

EXAMPLE 4

Spray Application to Soil Around Vegetative Material

The effect of applying metham as a spray to soil surrounding a newly planted reproductive vegetative plant part was determined as follows. An aqueous solution was prepared containing 2286 ppm of metham by dry weight of active ingredient. A greenhouse growing medium (Rediearth plus vermiculite 50:50 mix) was placed in 15.2 cm plastic pots, one pot for each replicate. A furrow was prepared in each pot for receiving a potato seed piece. The aqueous solution of metham was sprayed into the furrow, followed by planting of a potato seed piece in the furrow and then a second application of the aqueous metham solution over the planted seed piece. The rate of metham applied in this manner was varied by applying varying total amounts of liquid, with rates of application listed in Table 4 as weight of metham (by dry weight of active ingredient) per unit area or length of row treated. Four replicates were made at each treatment level. After planting, the potatoes were grown in a greenhouse for 34 days and then harvested. The average green weight (above ground parts) and tuber weight was determined as shown in Table 4.

TABLE 4

| Applicaton Rate | | Weight (grams) | |
|---|---|---|---|
| Grams/ sq. meter | Ounces/ 1000 ft row** | Vines | Tubers |
| 0 | 0.824 | 88.7 | 72.7 |
| 0.503 | 1.650 | 96.5 | 85.5 |
| 1.007 | 2.015 | 104.7 | 78.2 |
| 2.015 | 3.022 | 92.5 | 71.7 |
| 3.022 | 4.951 | 47.9 | 52.0 |

EXAMPLE 5

Post-Planting Drench Application

The effect of applying metham as a post-plant drench for the control of pests in a vegetative reproductive structure was determined by planting iris bulbs in 15.2 cm pots containing a greenhouse growing medium (perlite, vermiculite and peat moss). Immediately after planting, approximately 1.3 cm (0.51 inches) of an aqueous solution metham was applied to each pot. The concentration of metham in the aqueous solution was varied from 304 to 2438 ppm of metham by dry weight. Four replicates at each treatment level were made. The iris plants were grown in a greenhouse in Skagit County, Wash., U.S.A., for 66 days, harvested, and analyzed for average green weight and presence of nematodes, as shown in Table 5. The nematode value is given as the average number of *Ditylenchus destructor* recovered from one gram of bulb tissue.

TABLE 5

| Application Rate g/ meter$^2$ | Top weight | Nematodes |
|---|---|---|
| 0 | 25.8 | 848 |
| 3.952 | 25.1 | 798 |
| 7.917 | 23.6 | 158 |
| 15.847 | 24.4 | 64 |
| 31.694 | 23.8 | 24 |

EXAMPLE 6

Drench To Soil Surrounding Living Plants

Metham was applied in approximately 2.5 cm of water at concentrations ranging from 38.1 to 381 ppm of aqueous metham as a drench on soil containing established grass (turf type) in a 10 cm plastic pot. Each treatment was replicated 5 times. The grass was grown in a greenhouse and then harvested by clipping over a period of about 7 weeks. The data are presented in Table 6 as the average green weight of grass clippings harvested from each treatment by date. Rates of application are listed as weight of metham per unit of area treated.

TABLE 6

| Rate of Application | | Weight at harvest by date (g) | | | |
|---|---|---|---|---|---|
| g/meter sq | Pounds/Acre equivalent | 1/6 | 12/20 | 1/2 | Total |
| 0 | 0 | 9 | 13 | 2 | 24 |
| 0.952 | 8.51 | 13 | 23 | 2 | 38 |
| 1.905 | 10.03 | 46 | 150 | 9 | 204 |
| 3.810 | 34.07 | 27 | 22 | 7 | 56 |
| 5.715 | 51.11 | 11 | 36 | 4 | 51 |
| 7.620 | 68.15 | 25 | 16 | 10 | 51 |
| 9.529 | 85.23 | 30 | 63 | 26 | 119 |

Rates of application calculated on application of 2.5 cm of water per square meter or acre of land.

EXAMPLE 7

Phytotoxicity to Living Plants

The phytotoxicity of metham to Cotoneaster when applied as a drench to plants growing in one gallon containers was determined by applying aqueous solutions containing varying amounts of metham to soil in the containers in which healthy Cotoneaster plants were growing. The rates of application were varied as listed in Table 7 in PPM of metham aqueous solution, and applied in 250 ml of liquid per container, allowing for some of the aqueous metham solution to leach from the containers. After 72 days, the plant foliage was analyzed, as shown in Table 7.

TABLE 7

| Application Rate | Phytotoxicity rating | | |
|---|---|---|---|
| (PPM metham) | rep 1 | rep 2 | rep 3 |
| 0 | 1 | 1 | 1 |
| 57.1 | 1 | 1 | 1 |
| 114.3 | 1 | 2 | 1 |
| 228.6 | 1 | 2 | 2 |
| 342.9 | 3 | 2 | 2 |

Toxicity readings:
1 = normal growth
2 = slight foliage discoloration
3 = marked foliage discoloration
4 = death of part or all of plant Greenhouse assay of metham treated soil and laboratory assay of soil has indicated kill of most of the soilborne plant pathogens at levels of 50 to 350 ppm of metham by dry weight of active ingredient in aqueous solution.

While the invention has been described in connection with certain illustrative and presently preferred embodiments, various modifications will be apparent to those skilled in the art. Any such modifications are intended to be within the scope of the appended claims, except insofar as precluded by the prior art.

What is claimed is:

1. A method of enhancing plant growth in a plant bed, comprising treating the soil in the plant bed with a fungicidally effective amount of metham at or after the time of planting of seed or vegetative material in the plant bed, said fungicidally effective amount being insufficient to retard growth of a plant from the seed or vegetative material.

2. The method of claim 1, wherein the soil is treated with the metham by applying an aqueous solution of metham in a seed furrow of the plant bed at or after the time of planting of the seed or vegetative material in the plant bed.

3. The method of claim 2, wherein the aqueous solution is applied at a rate equivalent to about 0.003 to about 1.0 g of metham by dry weight of active ingredient per meter of furrow.

4. The method of claim 3 wherein the aqueous solution is dripped into the seed furrow at or after the time of planting of the seed or vegetative material.

5. The method of claim 1, wherein the soil is treated with the metham by injecting an aqueous solution of metham into the soil beneath the seed or vegetative material at or after the time of planting of the seed or vegetative material.

6. The method of claim 5, wherein the aqueous solution is injected in the soil at a rate equivalent to about 0.015 to about 1.5 g of metham by dry weight of active ingredient per linear meter of plant row.

7. The method of claim 6, wherein the aqueous solution is injected into the soil at a depth up to about 20 cm beneath the seed or vegetative material.

8. The method of claim 1 wherein the soil is treated with the metham by drenching the soil with an aqueous solution comprising metham.

9. The method of claim 8 wherein the soil is drenched with the aqueous solution at a rate equivalent to about 30 to about 2,500 ppm of metham by dry weight of active ingredient.

10. A method of enhancing plant growth in a plant bed comprising applying an aqueous solution of metham to soil in a seed furrow of the plant bed at or after the time of planting seed or vegetative material in the furrow, at a rate equivalent to about 0.003 to about 1.0 g of metham by dry weight of active ingredient per meter of furrow.

11. A method of enhancing plant growth in a plant bed comprising injecting an aqueous solution of metham into soil in a seed furrow of the plant bed at or after the time of planting seed or vegetative material in the furrow, at a rate equivalent to about 0.015 to about 1.5 g of metham by dry weight of active ingredient per linear meter of plant row.

12. A method of enhancing plant growth in a plant bed comprising drenching soil of the plant bed at or after the time of planting seed or vegetative material in the plant bed with an aqueous solution of metham at a rate equivalent to about 30 to about 2,500 ppm of metham by dry weight of active ingredient.

* * * * *

UNITED STATES PATENT AND TRADEMARK OFFICE
CERTIFICATE OF CORRECTION

PATENT NO. : 4,994,487                                      Page 1 of 2

DATED      : February 19, 1991

INVENTOR(S) : William A. Haglund

It is certified that error appears in the above-identified patent and that said Letters Patent is hereby corrected as shown below:

| Column | Line | |
|---|---|---|
| [56] (under "Other Publications") | | "User" should be --Use-- |
| 1 | 13 | "know" should be --known-- |
| 1 | 31&32 | "in-gredient)per" should be --ingredient) per-- |
| 1 | 51 | "776,922" should be --2,776,922-- |
| 4 (line 6 of Table 1) | 53 | "821" should be --820-- |
| 5 (Table 2) | 30 | "19 seeds" should be --10 seeds-- |
| 6 (Table 14) | 29 | "Applicaton" should be --Application-- |
| 7 (line 4 of Table 6) | 19 | "1/6" should be --12/6-- |
| 7 (line 4 of Table 6) | 19 | "1/2" should be --1/25-- |

UNITED STATES PATENT AND TRADEMARK OFFICE
CERTIFICATE OF CORRECTION

PATENT NO. : 4,994,487

DATED : February 19, 1991

INVENTOR(S) : William A. Haglund

It is certified that error appears in the above-identified patent and that said Letters Patent is hereby corrected as shown below:

| Column | Line | | |
|---|---|---|---|
| 8 | 31 | (Claim 6, line 3) | "abaut" should be --about--. |

Signed and Sealed this

Sixth Day of October, 1992

Attest:

DOUGLAS B. COMER

Attesting Officer     Acting Commissioner of Patents and Trademarks